United States Patent
Azimi (10) Patent No.: US 9,161,697 B2
(45) Date of Patent: Oct. 20, 2015

(54) SYSTEM FOR MEASURING AND RECORDING A USER'S VITAL SIGNS

(71) Applicant: DynoSense Corp., Sunnyvale, CA (US)

(72) Inventor: Saeed Azimi, Los Gatos, CA (US)

(73) Assignee: DYNOSENSE, CORP., Sunnyvale, CA (US)

( * ) Notice: Subject to any disclaimer, the term of this patent is extended or adjusted under 35 U.S.C. 154(b) by 132 days.

(21) Appl. No.: 13/961,441

(22) Filed: Aug. 7, 2013

(65) Prior Publication Data

US 2015/0045629 A1    Feb. 12, 2015

(51) Int. Cl.
| | |
|---|---|
| *A61B 5/0205* | (2006.01) |
| *A61B 5/0402* | (2006.01) |
| *A61B 5/1455* | (2006.01) |
| *A61B 5/00* | (2006.01) |
| *A61B 5/021* | (2006.01) |
| *A61B 5/11* | (2006.01) |
| *A61B 5/145* | (2006.01) |

(52) U.S. Cl.
CPC ........... *A61B 5/02055* (2013.01); *A61B 5/0022* (2013.01); *A61B 5/0205* (2013.01); *A61B 5/02125* (2013.01); *A61B 5/0402* (2013.01); *A61B 5/1118* (2013.01); *A61B 5/1455* (2013.01); *A61B 5/14507* (2013.01); *A61B 5/14551* (2013.01); *A61B 5/682* (2013.01); *A61B 5/6826* (2013.01); *A61B 5/742* (2013.01); *A61B 2560/0406* (2013.01); *A61B 2562/06* (2013.01)

(58) Field of Classification Search
CPC .. A61B 5/0022; A61B 5/0205; A61B 5/0402; A61B 5/0404; A61B 5/682; A61B 5/742; A61B 5/1112; A61B 5/1118; A61B 5/1455; A61B 5/02055; A61B 5/02125; A61B 5/6826; A61B 5/14507; A61B 5/14551; A61B 5/01; A61B 2560/0406; A61B 2562/06
USPC .................................. 600/300–301
See application file for complete search history.

(56) References Cited

U.S. PATENT DOCUMENTS

| | | | | |
|---|---|---|---|---|
| 8,133,176 B2* | 3/2012 | Porges et al. | ................. | 600/300 |
| 2010/0311003 A1* | 12/2010 | Kozlov | ............................. | 433/2 |
| 2012/0172679 A1* | 7/2012 | Logan et al. | .................. | 600/301 |
| 2013/0035602 A1* | 2/2013 | Gerner | ......................... | 600/484 |
| 2013/0253286 A1* | 9/2013 | Fridman | ...................... | 600/301 |

FOREIGN PATENT DOCUMENTS

WO    WO2012027648 A2 *   3/2012   ........... A61B 5/0205

* cited by examiner

*Primary Examiner* — Gary Jackson
*Assistant Examiner* — Boniface N Nganga
(74) *Attorney, Agent, or Firm* — Plager Schack LLP (57) ABSTRACT

A system for measuring and recording data pertaining to a user's vital signs in response to a single action by the user is provided. The system includes a base unit with a computer system, metallic layers affixed to a first side face and a bottom face of the base unit, an aperture, and a flexible shaft extending from the bottom face of the base, and an extension member pivotably mounted to a second side face of the base unit. The system receives the user's thumb on the metallic layer located on the first side face, index finger between the base unit and the extension member, lips on the bottom face metallic layer and tongue above the flexible shaft to capture the vital signs data and communicate the data to the remote location.

10 Claims, 10 Drawing Sheets

SYSTEM FOR MEASURING AND RECORDING A USER'S VITAL SIGNS

BACKGROUND

The embodiments herein relate generally to systems for measuring and recording a body's vital signs such as blood oxygen levels, respiratory characteristics, heart electrical signatures (electrocardiography or ECG), heart rate, blood pressure and temperature for health monitoring applications.

Currently there exist several systems that use multiple sensors connected to a single base unit, which is able to collectively measure all vital signs. These integrated units still require a user to connect two or more sensors to a particular location on the body. For example, a conventional pulse oximetry system used for the measurement of blood oxygen comprises a sensor attached to a user's finger, an oral thermometer requires placement under the tongue or arm, an infrared thermometer is placed in the ear canal, an ECG sensor requires two probes placed across the heart, and most blood pressure monitors use either auscultatory or oscillometric methods, which require a cuff to be worn on the user's arm. These systems have limitations because they are bulky or heavily power dependent and/or they require multiple attachments and actions by the user in order to measure and record the vital signs data.

As such, there is a need in the industry for a system that can detect and record all critical vital signs with a single action by the user.

SUMMARY

A system for measuring and recording data pertaining to a user's vital signs in response to a single action by the user, the system being configured to analyze and communicate the data to a remote location is provided. The system comprises a base unit comprising a computer system, metallic layers affixed to a first side face and a bottom face of the base unit, an aperture, and a flexible shaft extending from the bottom face of the base, and an extension member pivotably mounted to a second side face of the base unit, wherein the system is configured to receive the user's thumb on the metallic layer located on the first side face, index finger between the base unit and the extension member, lips on the bottom face metallic layer and tongue above the flexible shaft to capture the vital signs data and communicate the data to the remote location.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
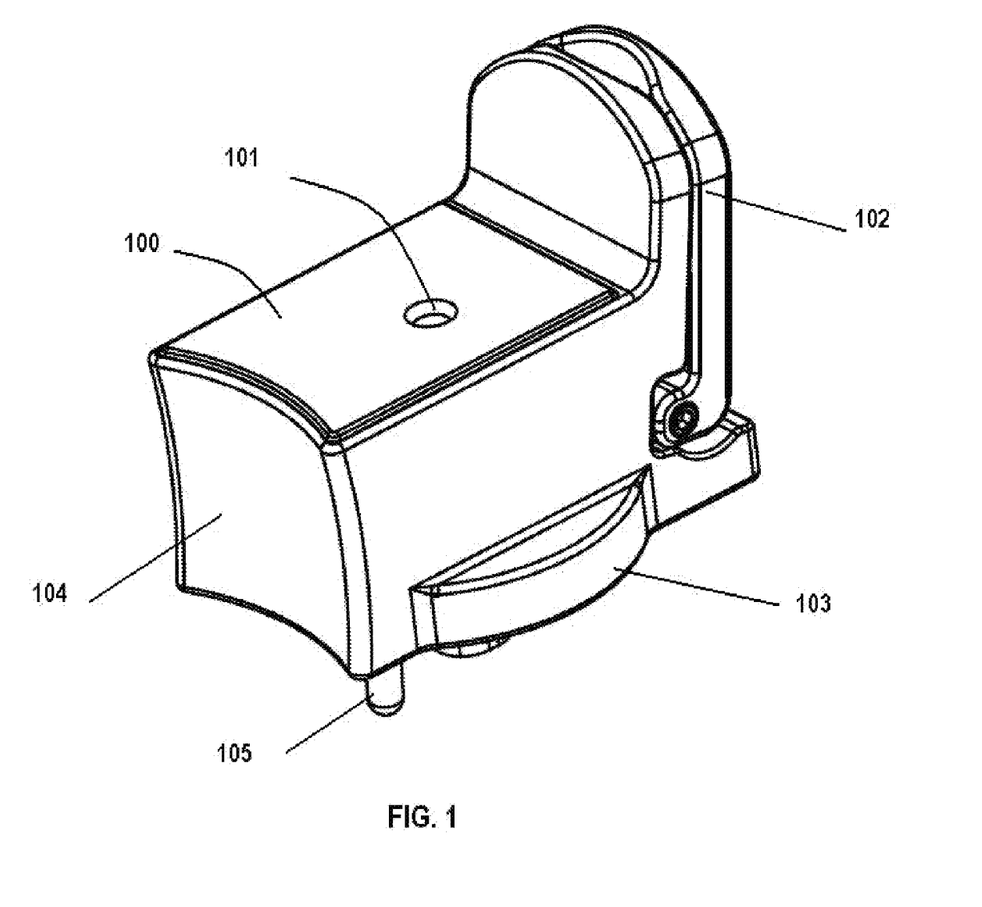
FIG. 1 depicts a perspective view of certain embodiments of the invention.
Figure 2:
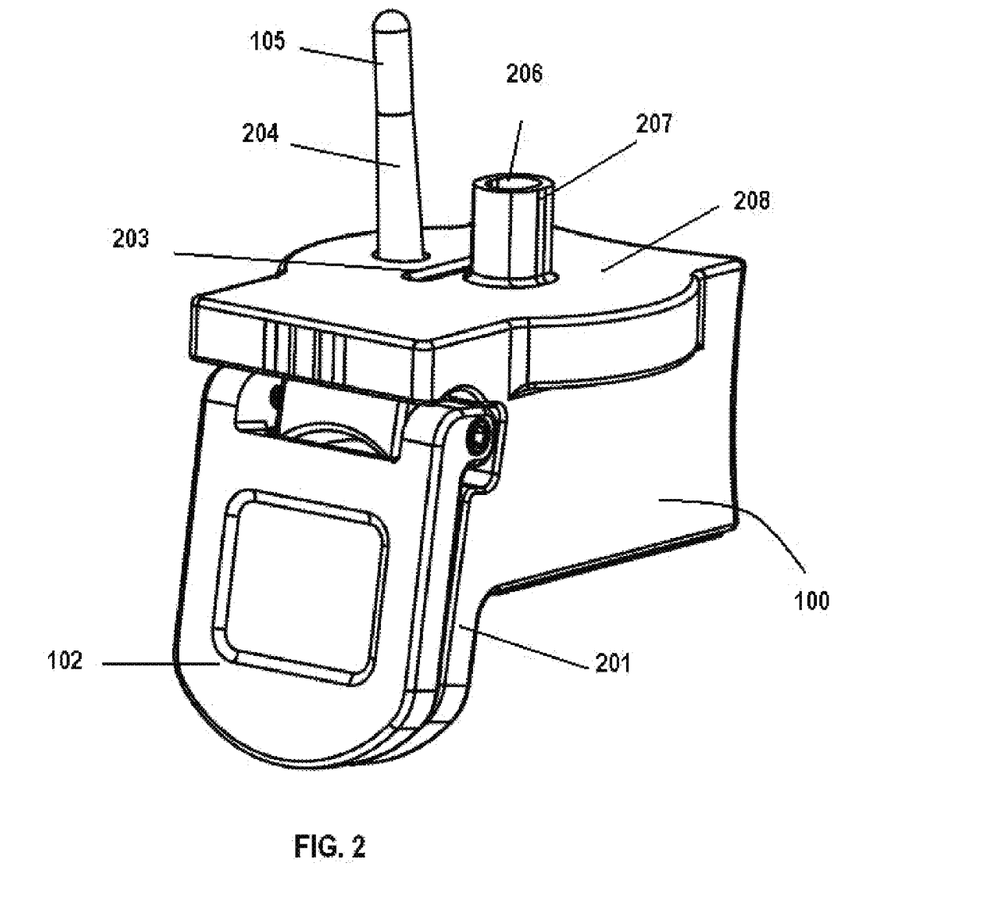
FIG. 2 depicts a perspective view of certain embodiments of the invention.
Figure 3:
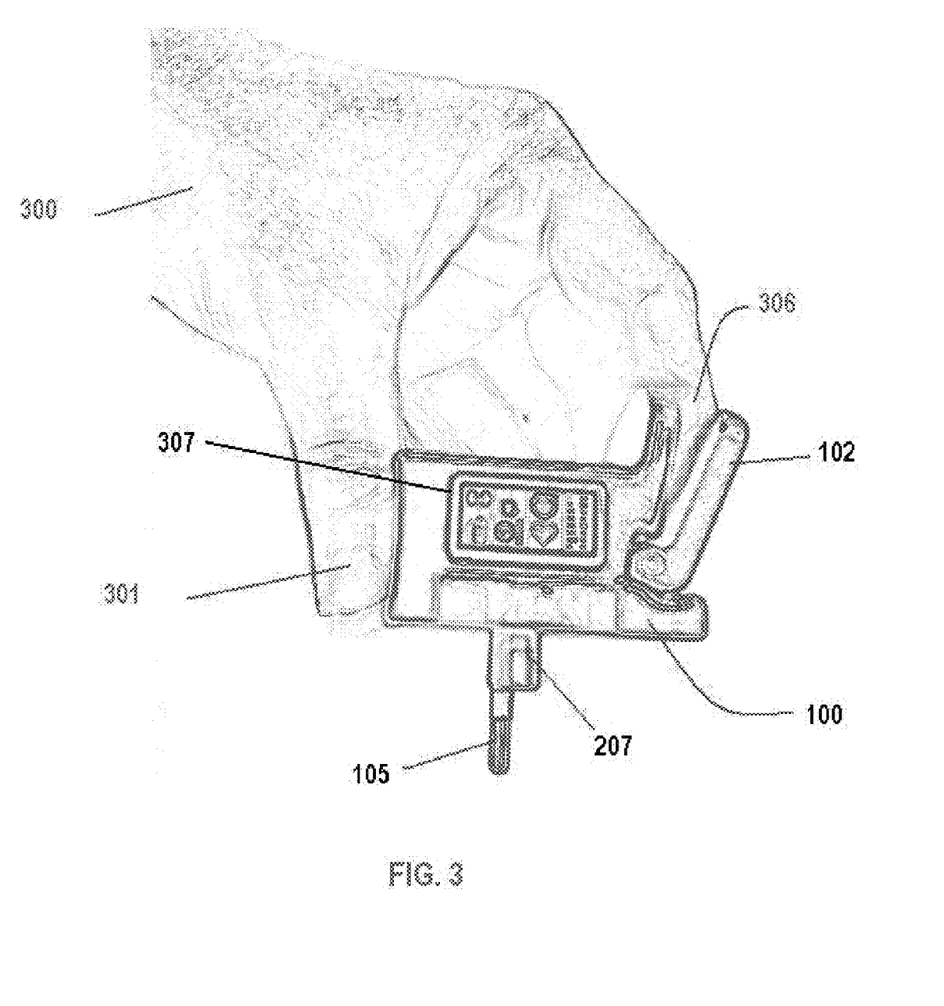
FIG. 3 depicts a side view of certain embodiments of the invention in use.

FIGS. 1-3 depict certain embodiments of the system for measuring a user's vital signs. The system 100 comprises a base unit comprising aperture 101, extension member 102, interior housing 103 comprising a computer system, contoured metallic pad 104, sensing tip 105, base unit extension 201, tongue resting area 203, flexible shaft 204, aperture (air opening) 206, air shaft 207, bottom metallic layer 208 and touch screen 307. Extension member 102 may be pivotably mounted to base unit extension 201 by any known components in the field such as a compression spring.

In certain embodiments of the invention, a first LED device is attached to extension member 102 and a second LED device is attached to base unit extension 201. These LED devices may comprise any known components in the field such as lights or detectors, which may comprise photoplethysmographs (PPG) or plethysmographs. One common use of photoplethysmography can be found in pulse oximeters, which determine the oxygen saturation of arterial blood and measures the change in the volume of arterial blood with each pulse beat. Pulse oximeter devices contain two light emitting diodes: one in the red band of light (660 nanometers) and one in the infrared band of light (940 nanometers). Oxyhemoglobin absorbs infrared light while deoxyhemoglobin absorbs visible red light. Pulse oximeter devices also contain sensors that detect the ratio of red/infrared absorption several hundred times per second. A preferred algorithm for calculating the absorption is derived from the Beer-Lambert Law, which determines the transmitted light from the incident light multiplied by the exponential of the negative of the product of the distance through the medium, the concentration of the solute and the extinction coefficient of the solute.

Figure 4:
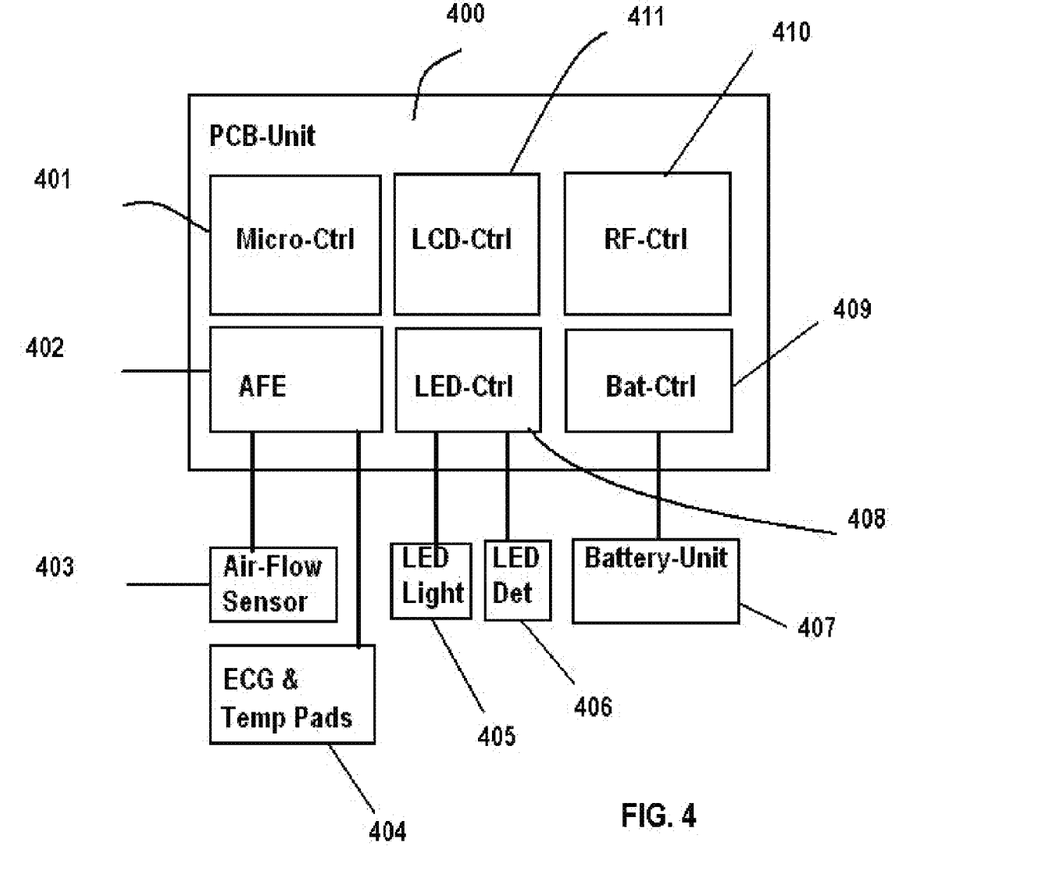
FIG. 4 depicts a block diagram of a computer system of certain embodiments of the invention.

FIG. 4 depicts the computer system, which comprises PCB-Unit 400, processor 401, Analog Front End (AFE) unit 402, which provides analog filtering, biasing and digitization of Air-Flow Sensor 403, which detects the user's breathing and acoustic sounds from the body. AFE unit 402 also provides analog filtering, biasing and digitization of ECG and Temperature Pads 404 located at metallic pad 104 and bottom metallic layer 208. LED-Controller unit 408 provides filtering, biasing and digitization of LED-Light 405 and LED-Detector 406 placed on extension member 102 and base unit extension 201, or vice versa, for detecting data related to a photoplethysmograph (PPG). Battery-Controller unit 409 provides power for all electronics of the system from battery source 407. RF-Controller 410 provides a wireless connection for transmitting and receiving data to system 100. LCD-Controller 411 displays information and receives an input from a user on touch screen 307.

Figure 5:
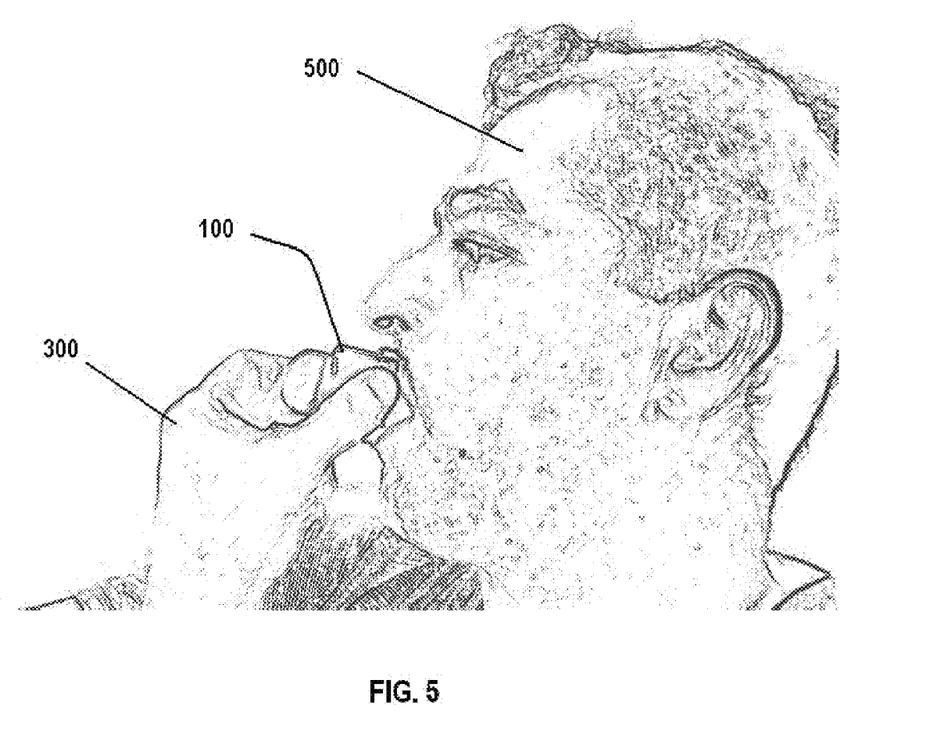
FIG. 5 depicts a side view of certain embodiments of the invention in use.
Figure 6:
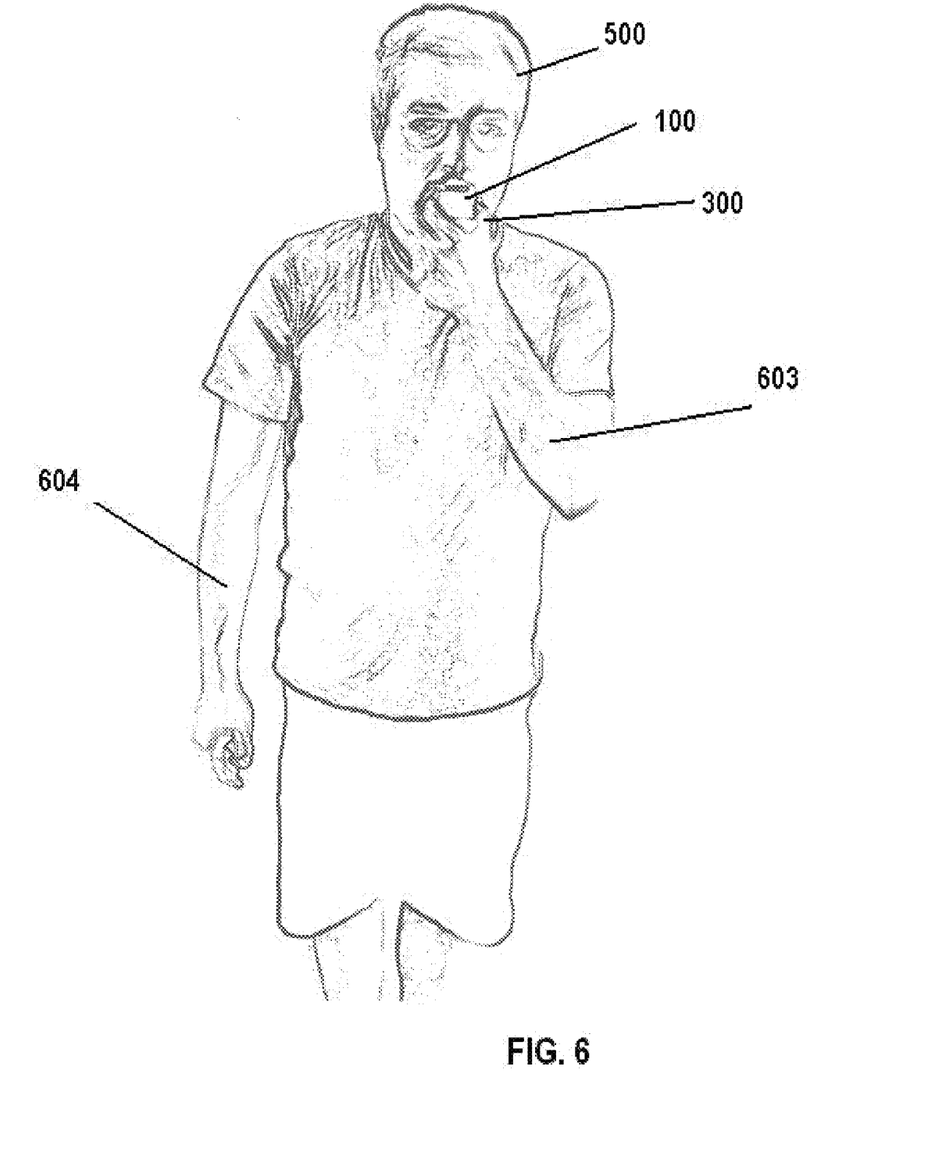
FIG. 6 depicts a front view of certain embodiments of the invention in use.

FIGS. 3 and 5-6 depict certain embodiments of the invention in use. A user 500 uses left hand 300 to hold system 100. The user's left thumb 301 is placed on contoured metallic pad 104 and left index finger 306 is placed between extension member 102 and base unit extension 201. System 100 is placed inside the user's mouth while held by left hand 300 such that sensing tip 105 on flexible shaft 204 is under the user's tongue below air shaft 207 with the tongue touching (or resting) on tongue resting area 203. In this position, air opening 206 is above the user's tongue and the lips are placed on bottom metallic layer 208 such that breathing is accomplished through the user's nose via air rushing through apertures 101 and 206.

Figure 7:
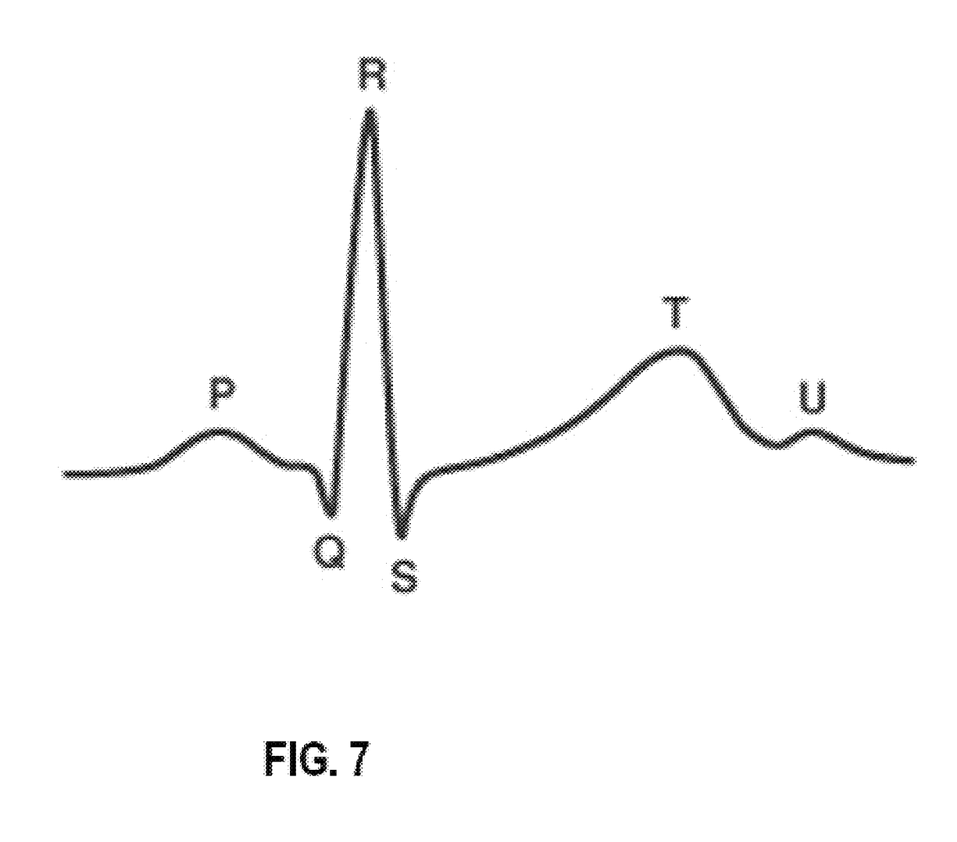
FIG. 7 depicts an electrocardiography waveform analyzed in certain embodiments of the invention.

In this setup, the computer system of system 100 senses electrical signals between thumb 301 placed on metallic pad 104 and bottom metallic layer 208 to construct an ECG signal as shown in FIG. 7. The computer system then calculates all heart related data from the ECG signal of FIG. 7, also referred to as a "QRS" complex wave. As the user breathes, the flow of air is sensed by the computer system by the amount of air rushing in and out of apertures 101 and 206, therefore yielding respiratory data. Sensing tip 105 measures the user's body temperature under the tongue. The LED detector measures data related to a PPG based on the reflection of LED light when the user's left index finger 306 is placed between extension member 102 and base unit extension 201. In this configuration, the index finger is placed between LED-Light 405 and LED-Detector 406.

Figure 8:
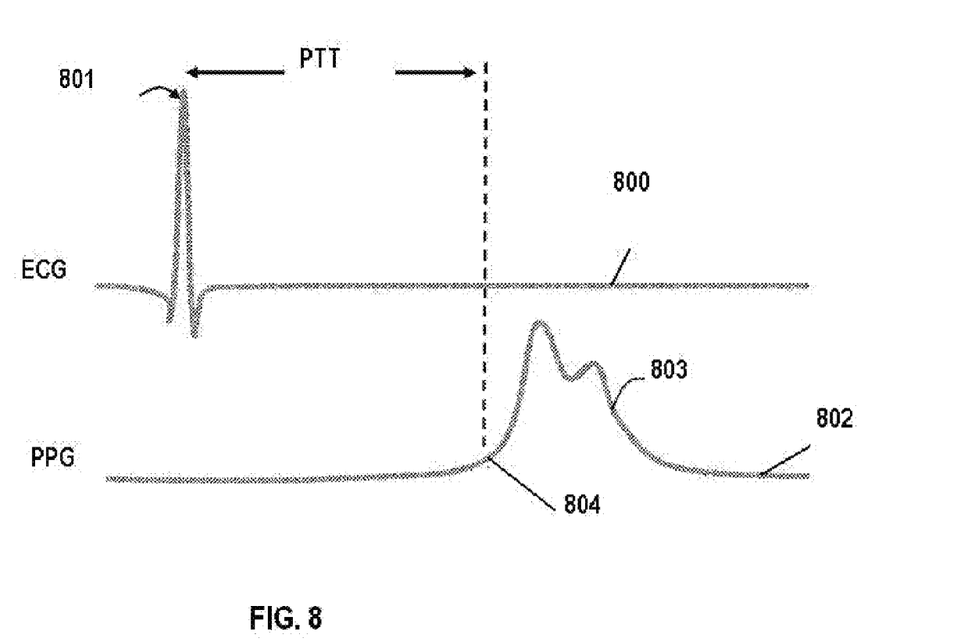
FIG. 8 depicts a series of electrocardiography waveforms analyzed in certain embodiments of the invention.

From constructed ECG signal 800 and PPG signal 802 it is then possible to construct the Pulse Transit Time ("PTT") shown in FIG. 8. PTT, defined as the transit time for a pressure pulse launched by a heartbeat in a patient's arterial system, has been shown in the prior art to correlate to both systolic and diastolic blood pressure. The QRS complex 800 indicates an initial depolarization of ventricles within the heart and, informally, marks the beginning of the heartbeat 801 and a pressure pulse that follows. Pulse oximetry is measured as described above on the user's left index finger. Time-dependent features of the optical waveform indicate both pulse rate and a volumetric absorbance change in an underlying artery in the finger caused by the propagating pressure pulse.

PTT measurements determine the time separating a maximum point on the QRS complex (indicating the peak of ventricular depolarization) 801 and a foot of the optical waveform 804 (indicating beginning of the pressure pulse) with 803 indicating the trailing end. PTT depends primarily on arterial compliance, the propagation distance of the pressure pulse (which is closely approximated by the patient's arm length 603 or 604), and blood pressure. To account for patient-dependent properties, such as arterial compliance, PTT-based measurements of blood pressure are 'calibrated' using a conventional blood pressure cuff. During the calibration process the blood pressure cuff is applied to the patient, used to make one or more blood pressure measurements, and then removed. Going forward, the calibration blood pressure measurements are used, along with a change in PTT, to determine the patient's blood pressure and blood pressure variability. PTT typically relates inversely to blood pressure, i.e., a decrease in PTT indicates an increase in blood pressure.

Figure 9:
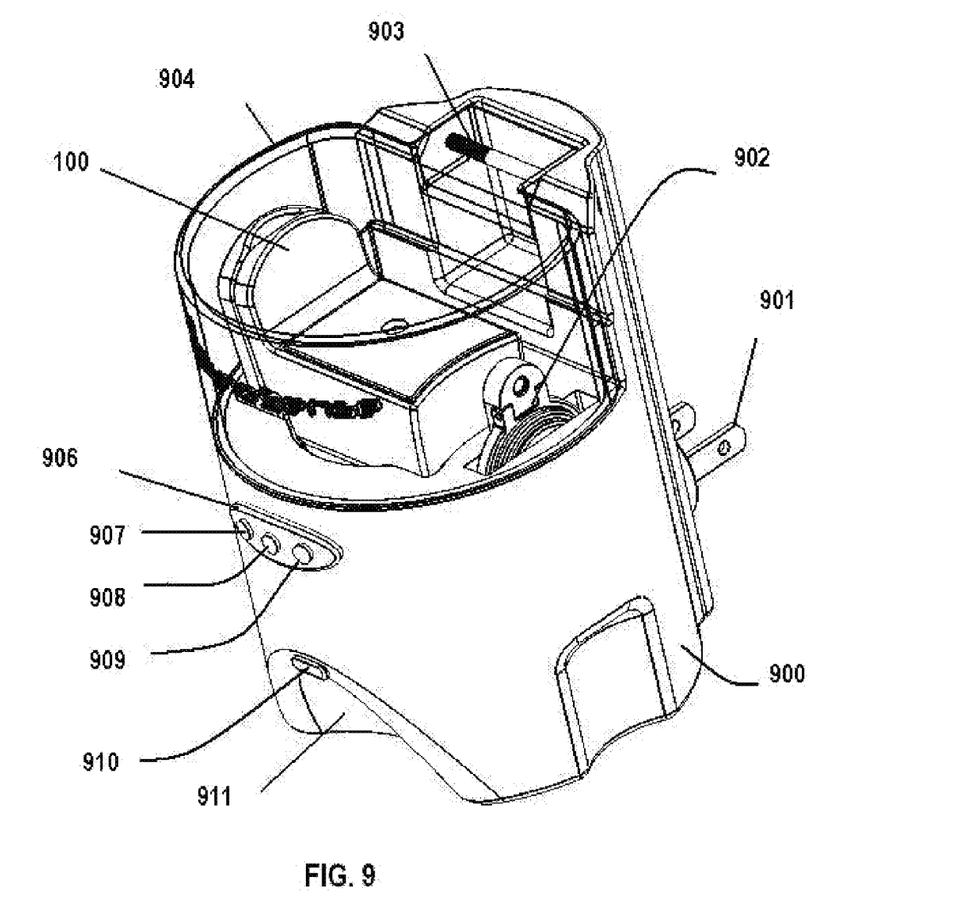
FIG. 9 depicts a perspective view of certain embodiments of the invention.

In certain embodiments of the invention, the vital signs data is displayed to the user on touch screen 307. In FIG. 9, cradle unit 900 charges system 100, cleans and sterilizes the system after each use. Cradle unit 900 can interact with a user using various LED colors 907, 908, 909 or 910, press button 906, as well as via voice command with built-in speaker and microphones 911. Furthermore, unit 900 has a wireless (Wi-Fi) or wired connection (Ethernet) to the Internet, which allows system 100 to communicate using short wavelength frequencies such as Bluetooth Radio. This configuration allows for a two way communication of cloud-based computer applications with system 100. Therefore, system 100 can transmit all vital signs data to the Internet and receive new programming from external cloud applications. Cradle unit 900 can also optionally communicate with other devices such as a weight scale, blood test kits, blood pressure cuff or other medical appliances.

Figure 10:
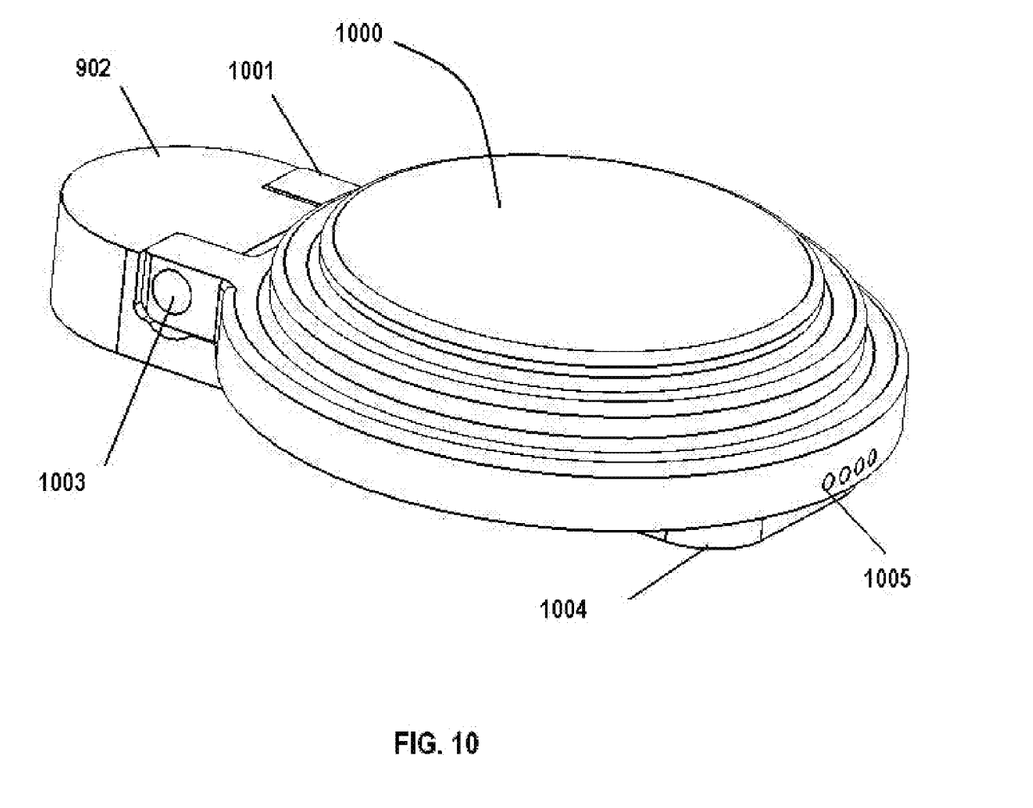
FIG. 10 depicts a perspective view of certain embodiments of the invention.

Cradle unit 900 gets power from wall outlet 901. A user places system 100 inside cradle unit 900 after each use by lifting lid 904 around pivot point 903. Optionally, there is activity tracking unit 902 that is also part of cradle unit 900. Referring to FIG. 10, activity tracker unit 902 comprises top face 1000, a motion sensor that is attached to the user's body using clips 1004 with pivot point 1003 and 1001 preferably on an undershirt for men and a bra-strap for women. The activity tracker unit 902 is charged using cradle unit 900 by being placed inside a slot in the cradle unit 900 via access ports 1005. The activity tracker also communicates with cradle unit 900 wirelessly. It shall be appreciated that activity tracker unit 902 may collect additional data about the user's body and/or activities.

In operation, as shown in FIG. 6, user 500 removes system 100 from cradle unit 900 (typically after brushing their teeth or at other times), and places it in the mouth with left hand 300 while relaxing right hand 604 typically in standing position while left arm 603 is in a bent position. The computer system calculates and captures all body vital signs accurately, typically in less than 30 seconds when an audible sound is heard instructing the user to remove system 100 from the mouth. System 100 is then washed and placed back into cradle unit 900. The user can selectively review the data on touch screen 307 or visit a website by logging into an account and reviewing the data.

In one embodiment, the system generates alerts and alarms if it detects that any values of the vital signs are outside the normal limits. The system may generate messages (e.g., email or SMS messages) containing such information to be sent to the doctor, the user, and/or any such person chosen by the user.

In an alternative embodiment, system 100 has access to body saliva samples during operation of sensing vital signs. Body saliva is similar to blood in many ways and therefore detectors can be developed to obtain, analyze and detect other non-vital sign data about the body such as glucose level, influenza A or B, alcohol or drug levels and DNA analyses.

It shall be appreciated that the components of the system described in several embodiments herein may comprise any known materials in the field such as metals and molded plastics, and be of any color, size and/or dimensions.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A system for measuring and recording data pertaining to a user's vital signs in response to a single action by the user, the system being configured to analyze and communicate the data to a remote location, the system comprising:

a base unit comprising a computer system, an aperture, a top face, a bottom face, a first side face and a second side face positioned opposite the first side face;

a first contoured metallic layer affixed to the first side face of the base unit and adapted to conform to contours of a thumb of the user;

a second metallic layer affixed to the bottom face of the base unit; a flexible shaft affixed to the bottom face of the base unit; and an extension member pivotably mounted to the second side face of the base unit; wherein the system is configured to receive the user's thumb on the first contoured metallic layer, an index finger between the base unit and the extension member, lips on the second metallic layer and tongue above the flexible shaft to capture the vital signs data and communicate the data to the remote location.

2. The system of claim 1, further comprising a display configured to receive an input from the user and display to the user vital signs data.

3. The system of claim 1, wherein the extension member comprises a light-emitting diode device configured to be used as a plethysmograph.

4. The system of claim 1, wherein the computer system is configured to transmit an alert to an entity if any values of the user's vital signs data are outside normal limits.

5. The system of claim 1, wherein the computer system generates an electrocardiography signal based on electrical signals detected by the metallic layers.

6. The system of claim 1, wherein the computer system detects airflow through the aperture based on a breath of the user and generates respiratory data based on the detected airflow.

7. The system of claim 1, further comprising a detector configured to measure and record data pertaining to the user's non-vital signs.

8. The system of claim 1, further comprising a cradle unit configured to store, clean and sterilize the base unit and the extension member.

9. The system of claim 8, further comprising an activity tracker unit configured to collect data pertaining to the user's activities.

10. The system of claim 8, wherein the cradle unit comprises a communication device configured to wirelessly communicate the vital signs data to the remote location and other devices.

* * * * *